United States Patent [19]

Weinberger

[11] Plant 4,893

[45] Oct. 5, 1982

[54] NECTARINE TREE

[75] Inventor: John H. Weinberger, Fresno, Calif.

[73] Assignee: Superior Farming Company, Bakersfield, Calif.

[21] Appl. No.: 224,164

[22] Filed: Jan. 12, 1981

[51] Int. Cl.[3] ..... A01H 5/00
[52] U.S. Cl. ..... Plt./41
[58] Field of Search ..... Plt./41

*Primary Examiner*—Robert E. Bagwill
*Attorney, Agent, or Firm*—Roger B. Webster

[57] ABSTRACT

A nectarine tree which is medium in size and vigor, upright-spreading, open, and round-topped; foliated with medium size, ovate, lanceolate, acutely pointed leaves having a crenate margin and alternate-irregular, medium size, reniform glands; flowers from appressed, pubescent buds of medium size and length; the flowers, of medium season, being large and pink; and is a regular and productive bearer of early-season, medium size, uniform, symmetrical, ovoid, freestone-semi-freestone fruit having yellow skin substantially overspread and blushed with red, and yellow flesh.

1 Drawing Figure

BACKGROUND OF THE VARIETY

1. Field of the Invention

In the conduct of an extensive plant breeding program—on behalf of a commercial farming company, and in such company's experimental orchard located near Fresno, Fresno County, Calif.—I have originated a substantial number of new and distinct varieties of fruit trees, and which include the present variety of nectarine tree.

2. Classification of the Variety

The present variety of nectarine tree is embraced by Class 41, Plants, of the U.S. Patent Office Manual of Classification.

3. Prior Varieties

Among existing varieties of nectarine trees which are known to me, and mentioned herein, is the May Grand (U.S. Plant Pat. No. 2,794).

ORIGIN OF THE VARIETY

The present variety of nectarine tree was originated by me as an open pollinated seedling of the May Grand nectarine. A number of such seedlings were grown to fruition, in the aforesaid experimental orchard, under careful and continuing observation by me; the present variety being a selection from such seedlings which evidenced commercial promise.

ASEXUAL REPRODUCTION OF THE VARIETY

Asexual reproduction of the variety was successfully accomplished, under my direction and in the aforesaid experimental orchard, by budding; such asexual reproductions, in maturity, having run true to the original tree in all respects.

SUMMARY OF VARIETY

The present variety of nectarine tree is—characteristically—medium in size and vigor, upright-spreading, open, and round-topped; foliated with medium size, ovate, lanceolate, acutely pointed leaves having a crenate margin and alternate-irregular, medium size, reniform glands; flowers from appressed, pubescent buds of medium size and length; the flowers, of medium season, being large and pink; and is a regular and productive bearer of early-season, medium size, uniform, symmetrical, ovoid, freestone-semi-freestone fruit having yellow skin substantially overspread and blushed with red, and yellow flesh.

The present variety of nectarine tree is further characterized in comparison to the May Grand nectarine, as follows:

The tree is more productive; the fruit is in harvest approximately one week later; the fruit base is broader and more rounded, usually with a larger, broader cavity; the sides or shoulders of the fruit are less abrupt and less slanted; and the fruit—absent the tendency of the May Grand to be flattened on the dorsal side—is more rounded in the length dimension and relatively shorter. In brief, the present variety of nectarine tree extends the harvest season of the May Grand type of fruit with fruit which is more rounded and hence of smoother configuration.

BRIEF DESCRIPTION OF THE DRAWING

The drawing is an illustration, by photographic reproduction in color, of a twig with leaves, and separate fruit; one fruit being half cut away to expose the flesh and stone.

DESCRIPTION OF THE VARIETY

The botanical details of this new and distinct variety of nectarine tree—with color definitions (except those in common color terms) referenced to Plochere Color System (in book form)—are as follows:

Tree:
- *Size.*—Medium.
- *Vigor.*—Medium.
- *Growth.*—Upright — spreading.
- *Density.*—Open.
- *Form.*—Round-topped.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.
- *Color.*—New wood: green, dull. Mature wood: brown.

Leaves:

*Size.*—Medium. Average length — 15.7 cm. Average width — 4.2 cm.
*Form.*—Ovate. Lanceolate. Acutely pointed.
*Thickness.*—Medium.
*Color.*—Medium green.
*Texture.*—Smooth.
*Margin.*—Crenate.
*Petiole.*—Medium length. Medium thickness.
*Glands.*—Average number — 3. Alternate — irregular. Medium size. Reniform. Green. Positioned distal on petiole, basal on blade.
*Stipules.*—Shed as leaves mature.

Flower buds:
*Size.*—Medium.
*Length.*—Medium.
*Form.*—Plump. Appressed. Pubescent.

Flowers:
*Date of full bloom.*—Mar. 5th, 1980. Medium, as compared with other varieties.
*Size.*—Large.
*Color.*—Pink.

Fruit:
*Maturity when described.*—Firm ripe — June 18th, 1980.
*Date of first picking.*—June 14th, 1980.
*Date of last picking.*—June 23rd, 1980.
*Size.*—Uniform. Medium. Average diameter axially — 6.1 cm. Average transversely in suture plane — 6.0 cm.
*Form.*—Uniform. Symmetrical. Ovid.
*Suture.*—A shallow inconspicuous line extending from base to beyond but discontinues at apex, with slight depression beyond pistil point.
*Ventral surface.*—Rounded slightly. Lipped throughout.
*Lips.*—Slightly unequal.
*Cavity.*—Rounded. Circular. Average depth — 8 mm. Average breadth — 17 mm.
*Base.*—Rounded.
*Apex.*—Short. Rounded.
*Pistil point.*—Apical.

Skin:
*Thickness.*—Medium.
*Texture.*—Medium.
*Tenacity.*—Tenacious to flesh.
*Tendency to crack.*—None in dry season.
*Color.*—Ground color — yellow (Plate 7 — No. 147 — Nasturtium). Blush color — red (Plate 17 — No. 385 — Crimson Glory).

*Down.*—Wanting.

Flesh:
*Color.*—Yellow. (Plate 7 — No. 147 — Nasturtium). Tinge of red near stone apex.
*Amygdalin.*—Wanting.
*Juice.*—Moderate. Rich.
*Texture.*—Medium. Melting.
*Fibers.*—Few. Fine. Tender.
*Ripens.*—Evenly.
*Flavor.*—Acid. Delicate.
*Aroma.*—Wanting.
*Eating quality.*—Best.

Stone:
*Type.*—Free to semi-free.
*Fibers.*—Short.
*Size.*—Medium. Average length — 39 mm. Average breadth — 26 mm. Average thickness — 20 mm.
*Form.*—Obovoid.
*Base.*—Straight.
*Hilum.*—Oval.
*Apex.*—Acuminate.
*Sides.*—Equal.
*Surface.*—Regularly furrowed near ventral edge toward apex. Ridged toward apex. Pitted from base to above center.
*Ridges.*—Rounded toward apex. Interrupted.
*Pits.*—Circular. Elongated.
*Ventral edge.*—Thick. Without wing throughout.
*Dorsal edge.*—Narrow. Shallow throughout.
*Color.*—Tan (Plate 7 — No. 146 — California Poppy).
*Tendency to split.*—Slight in wet — dry seasons.

Use: Market.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as shown and described, characterized in comparison to the May Grand nectarine by a tree which is more productive and fruit which is in harvest approximately one week later, the fruit being more rounded and of smoother configuration.

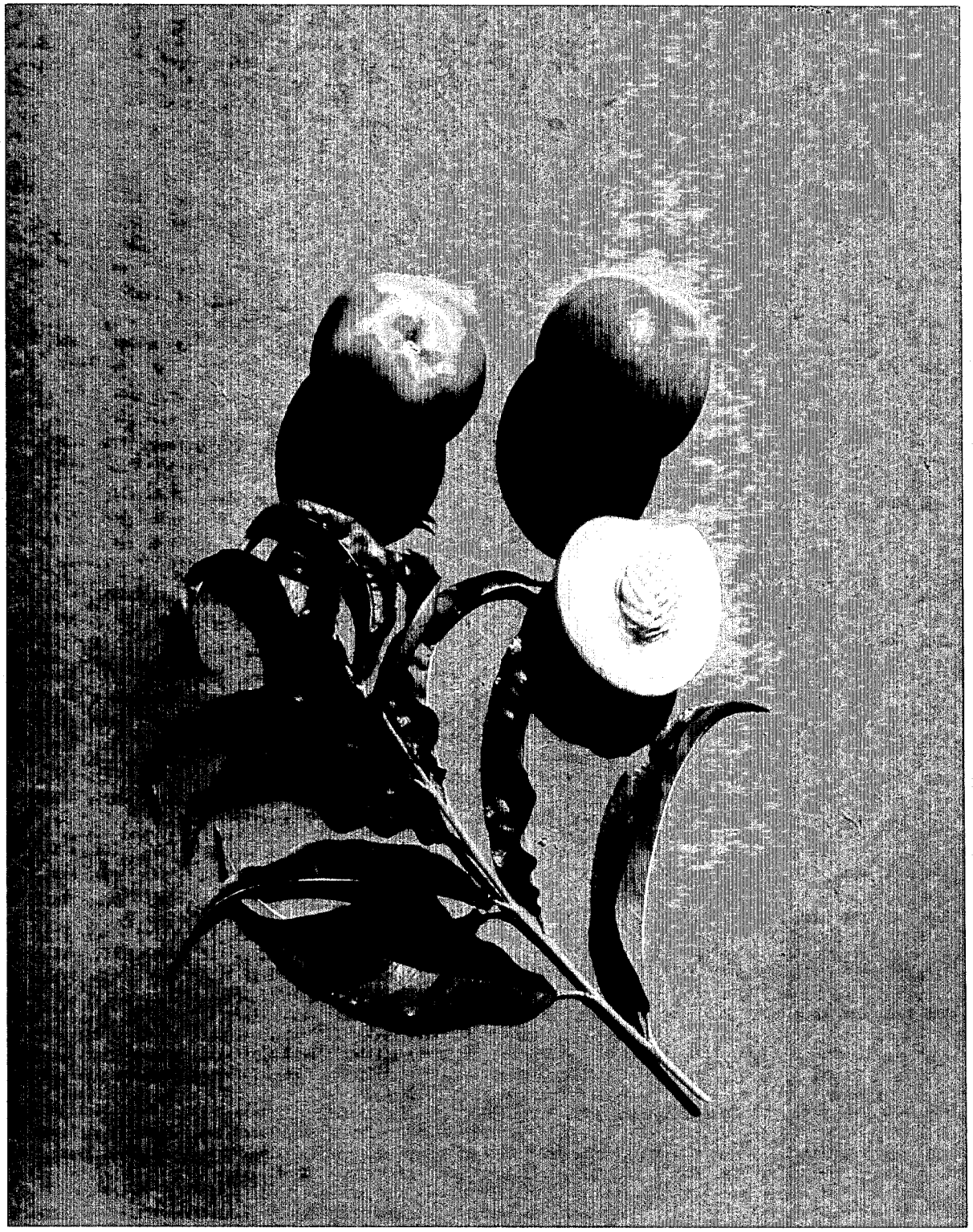

* * * * *